US00PP09174P

United States Patent [19]

Frederick et al.

[11] Patent Number: Plant 9,174

[45] Date of Patent: Jun. 20, 1995

[54] JUNIPER PLANT—'LOREE DAWN' VARIETY

[75] Inventors: Donald G. Frederick; Ada W. Frederick, both of Blairsville, Pa.

[73] Assignee: The Conard-Pyle Company, West Grove, Pa.

[21] Appl. No.: 298,050

[22] Filed: Aug. 30, 1994

[51] Int. Cl.[6] ..... A01H 5/00

[52] U.S. Cl. ..... Plt./50.2

[58] Field of Search ..... Plt. 50.2

[56] References Cited

U.S. PATENT DOCUMENTS

| | | | |
|---|---|---|---|
| P.P. 5,014 | 3/1983 | Girard | Plt./50.2 |
| P.P. 6,149 | 4/1988 | Strohsahl | Plt./50.2 |
| P.P. 8,202 | 4/1993 | Bakker | Plt./50.2 |

*Primary Examiner*—James R. Feyrer
*Attorney, Agent, or Firm*—Burns, Doane, Swecker & Mathis

[57] ABSTRACT

A new and distinct variety of *Juniperus chinensis* plant was discovered as a limb mutation among plants of the 'Pfitzeriana Aurea' variety. The new variety is slower growing than its parent and exhibits a more compact and more prostrate growth habit than 'Pfitzeriana Aurea'. The new variety exhibits very fine, cascading foliage and a brilliant gold color that is speckled throughout the plant (as illustrated). The new variety because of its distinct appearance is particularly suited for use as a foundation planting, as a landscape specimen, or as a decorative mass planting. The golden foliage coloration commonly persists throughout the summer and winter months whereas other golden junipers commonly assume a brownish-green coloration during the winter months. Slow growing and fine, lacy-textured plants requiring very little maintenance are provided which impart a vivid coloration to the landscape throughout the year.

2 Drawing Sheets

SUMMARY OF INVENTION

The present invention comprises a new and distinct variety of *Juniperus chinensis* that has been named the 'Loree Dawn' variety.

The new 'Loree Dawn' variety is a spontaneous mutation of unknown causation which was discovered and carefully preserved during the late 1970's in the course of plant selection work conducted at Blairsville, Pa., U.S.A. A single branch of a single plant of *Juniperus chinensis* 'Pfitzeriana Aurea' (non-patented in the United States) was found to exhibit a distinctive foliage appearance unlike that exhibited by all other plants grown in the area. The parent 'Pfitzeriana Aurea' plant sometimes is known as the 'Gold Tip'0 variety. Had we not discovered and preserved this new plant it would have been lost to mankind.

It was found that the new variety of *Juniperus chinensis:*

(a) grows more slowly than 'Pfitzeriana Aurea',
(b) exhibits an attractive, fine and lacy-textured, brilliant gold foliage that is deeper and more persistent than that of 'Pfitzeriana Aurea', and
(c) exhibits a more compact and more prostrate growth habit than that of 'Pfitzeriana Aurea'.

The golden foliage coloration is of a more vivid yellow than the typical golden *Juniperus chinensis,* such as 'Pfitzeriana Aurea'. The foliage is speckled in appearance throughout the plant. More specifically, the foliage color of the new variety is a speckled brilliant gold and bright green on a variegated background of frost blue, green and gold. The slow growth and prostrate growth habit of the new variety enables the grower to well retain the desired overall appearance of the planting over an extended period of time.

Mature plants propagated from the original mutation have reached a height of approximately 12 to 18 inches and a width of approximately 36 to 48 inches. The winter hardiness of the new variety has been confirmed at both Blairsville and West Grove, Pa., U.S.A.

The plants of this new variety have been found to retain excellent color with a bright, fresh appearance even during the winter months. The degree of color fading tends to be minimal to none. Also plants of the new variety undergo shearing well while still retaining an attractive appearance.

Asexual propagation of the new variety has been successfully carried out since 1984 at Blairsville and West Grove, Pa., U.S.A. Rooted cuttings have repeatedly demonstrated that the characteristics of the new variety as discussed herein are firmly fixed and are retained through successive generations of asexual propagation. For instance, the new variety can be readily propagated through the use of hardwood cuttings during the winter. Alternatively, during the summer cuttings of new growth can be placed under mist. The new asexually reproduced plants produced from cuttings have been found to grow vigorously, are true-to-type, and have encounted few problems from insects or diseases. There have been no observed reversions of the new variety to the parent variety during the entire period of its observation.

The new variety because of its distinctive foliage coloration, texture and growth habit, was found to be particulary suited for growing as a specimen plant, as a foundation planting, or as a decorative mass planting. It lends itself well to conventional production methods and cultural practices when grown either in field or in containers, and well meets the demands of the modern landscape. Dense compact finely-textured plants are provided that require little maintenance while imparting an attractive vivid coloration to the landscape throughout the entire year.

The new variety, in view of its novel combination of characteristics, can be readily distinguished from all other golden *Juniperus chinensis* such as 'Pfitzeriana Aurea'. For instance, the new variety exhibits a different golden coloration than 'Pfitzeriana Aurea'. The foliage of new variety is more speckled and flecked. The coloration is also more vivid and covers the entire plant. As stated, the golden foliage coloration commonly persists throughout the summer and winter months whereas other golden junipers commonly assume a brownish-green foliage coloration during the winter months. When the new variety is grown side-by-side with the 'Pfitzeriana Aurea' juniper and the 'Bakaurea' juniper (U.S. Plant Pat. No. 3,801), the differences in foliage coloration are readily apparent. Also, the speckled appearance of the foliage of the new variety is absent in the 'Gold Lace' variety (U.S. Plant Pat. No. 8,202).

BRIEF DESCRIPTION OF THE PHOTOGRAPHS

The accompanying photographs show as nearly true as it is reasonably possible to make the same in color illustrations of this character, typical specimens of the plant and plant parts of the new variety. The plants depicted in the photographs were grown in Blairsville, Pa., U.S.A.

FIG. 1.—illustrates the typical early summer appearance of young plants of the new variety on the right as compared to the appearnce of *Juniperus chinensis* 'Bakaurea' (U.S. Plant Pat. No. 3,801) on the left. A blue spruce is shown in the background.

FIG. 2.—illustrates the typical mid-summer appearance of the new variety at the center following two seasons of growth wherein the summer coloration can be contrasted to that of a typical blue juniper at the left.

FIG. 3.—illustrates a closer perspective view of the typical texture and summer coloration of the foliage of the new variety.

FIG. 4.—illustrates during early summer differences in typical foliage texture and coloration between *Juniperus chinensis* 'Pfitzeriana Aurea' on the left and the new variety on the right.

DETAILED DESCRIPTION

Figure 1:
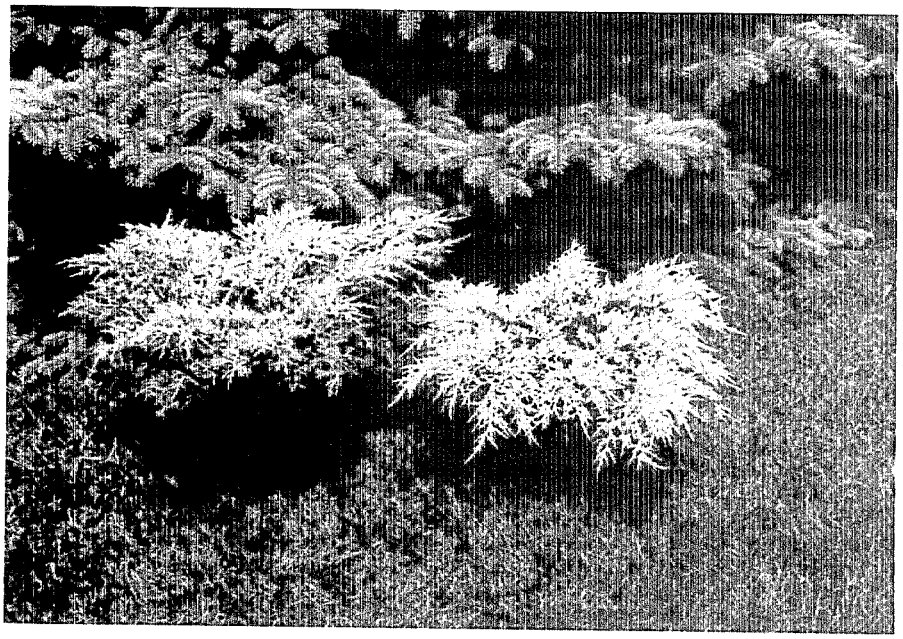
Figure 2:
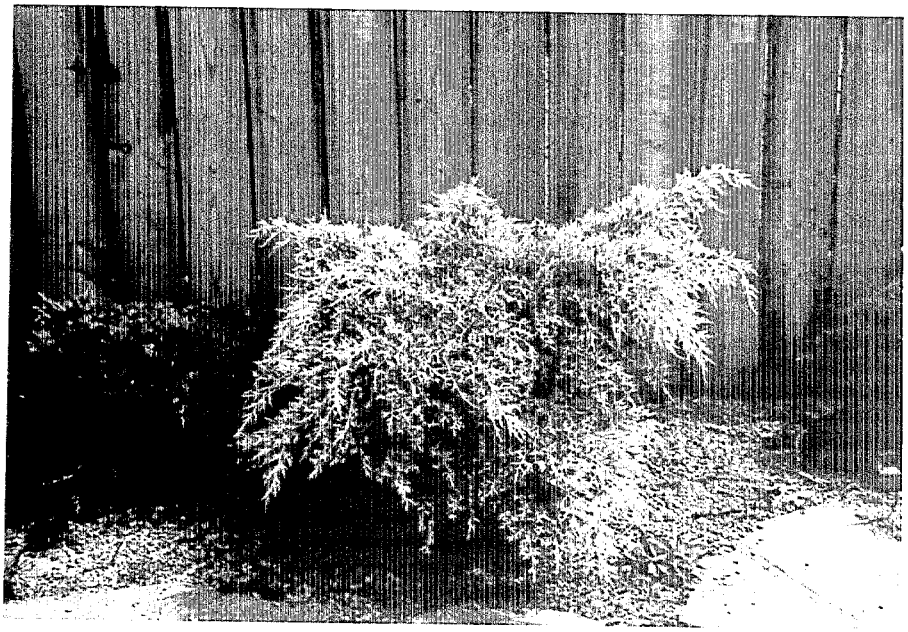
Figure 3:
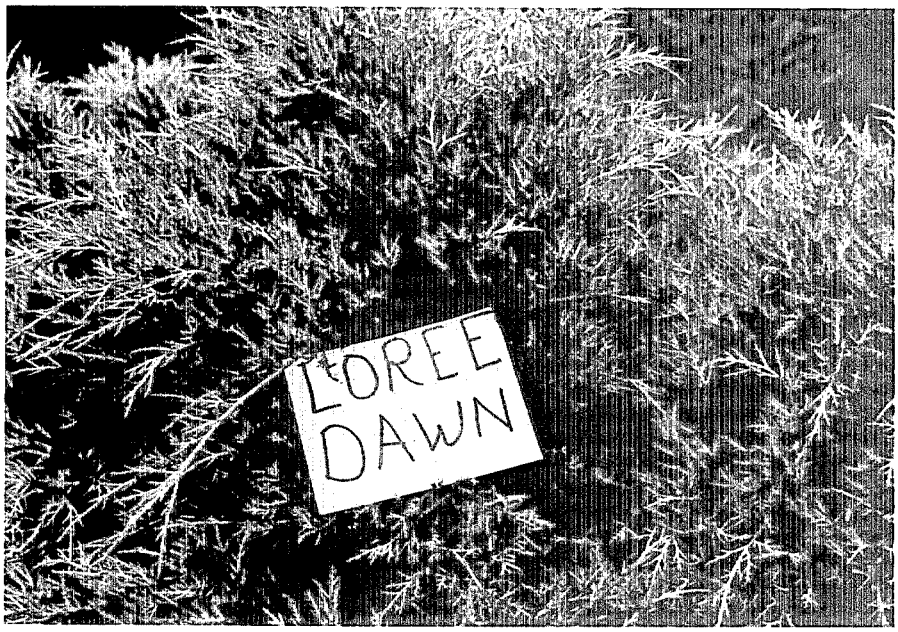
Figure 4:
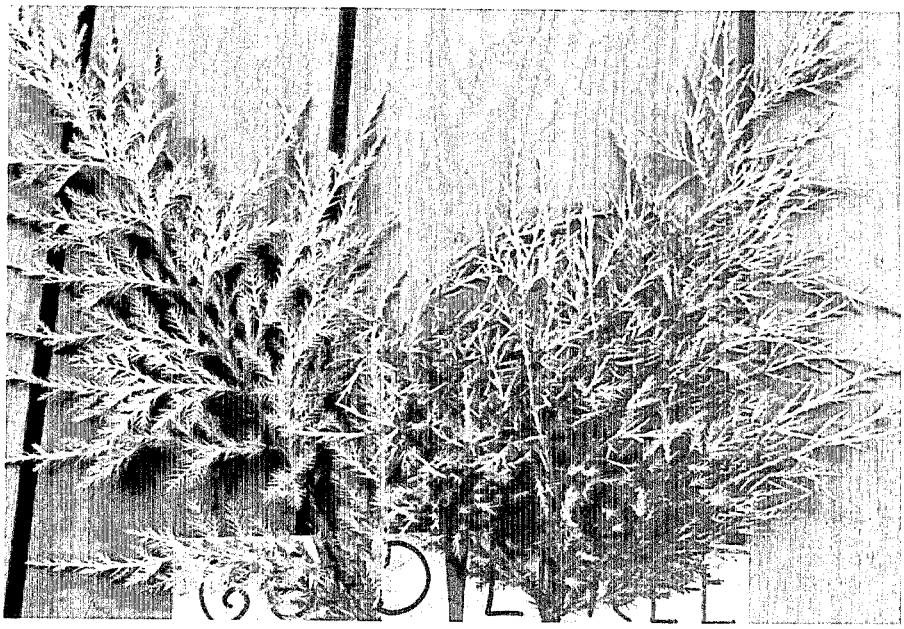

The chart used in the identification of colors described hereafter is the R.H.S. Colour Chart of The Royal Horticultural Society, London England. The plants described were grown in full sun during 1993 at West Grove, Pa., U.S.A.

Classification: *Juniperus chinensis, 'Loree Dawn' variety.*

Foliage:

*Type.*—Juvenile, needle and awl-shaped.

*Spring-summer color of new leaves at growing tips of primary and secondary branches.*—Upper side: Initially Yellow Group 12B, turning to Yellow Group 11B in early summer, and then turning to Yellow-Green Group 153D. Lower side: At point of attachment Yellow Group 7D in the spring and turning to Yellow-Green Group 154D. Tip of leaf: Yellow Group 2C in spring, and turning to Yellow Group 7A during the summer.

*General appearance of new leaves when unfolding during the spring.*—Upper side: Yellow Group 12B . Lower side: Yellow Group 10A. At point of attachment: Yellow Group 3C. At center of leaf: Yellow Group 3B.

*General appearance of foliage during the spring-*.—Upper side: Green-Yellow Group 1C, mixed with Yellow Group 5C. Lower side: Yellow Group 3B mixed with Green Group 143C.

*General appearance of foliage during early-summer-*.—Upper side: Yellow Group 3C mixed with Green-Yellow Group 1C. Lower side: Yellow Group 12B mixed with Green Group 137D.

*General appearance of foliage during late summer-*.—Upper side: Yellow Group 13B mixed with Green Group 138A. Lower side: Yellow Group 13C mixed with Green Group 138B.

*Winter color of tips of primary and secondary branches when exposed to weather.*—Upper side: Yellow-Orange group 14C. Lower side: Yellow-Orange Group 13B.

*Winter general appearance of foliage on the outside of the plant.*—Upper side: Greyed-Green Group 191B mixed with Yellow Group 13B and Yellow Group 12C. Lower side: Greyed-Green Group 191B mixed with Yellow Group 13B.

*Winter color of leaves on outside of plant when protected from the weather.*—Tips: Between Yellow-Orange Group 22A and Yellow-Orange Group 22B. On maturing wood: Greyed-Green Group 191A. On mature wood: Between Green Group 137C and Greyed-Green Group 191B.

Branches:

*Summer coloration.*—On growing tips of main branches: Yellow Group 11A. On side shoots of main branches: Yellow-Green Group 144C. On maturing wood: Yellow-Green Group 144C mixed with Brown Group 200C. On seconardy branches: Grey-Brown Group 199B.

*Winter coloration.*—On outer branches: Orange Group 24B mixed with Greyed-Orange Group 167C. On mature branches: Greyed-Green Group 191B mixed with Greyed Orange Group 177C.

*On old wood.*—Greyed-Green Group 191A mixed with Greyed-Orange Group 177C.

General appearance of entire plant:

*End of winter.*—At center of plant: Yellow Green Group 147B. At outer parts of plant: Green Group 139C.

*Mid spring.*—At center of plant: Green Group 139B mixed with Yellow Group 4B. At outer parts of plant: Yellow Group 4C.

*Summer.*—At center of plant: Between Yellow-Green Group 144B and Green Group 143B. At outer parts of plant: Yellow-Green Group 154D mixed with Yellow Group 8D.

We claim:

1. A new and distinct variety of *Juniperus chinensis* substantially as herein shown and described, which:

(a) grows more slowly than 'Pfitzeriana Aurea', (b) exhibits an attractive, fine and lacy-textured brilliant gold foliage that is deeper and more persistent than that of 'Pfitzeriana Aurea', and (c) exhibits a more compact and more prostrate growth habit than 'Pfitzeriana Aurea'.

* * * * *